US009999782B2

(12) United States Patent
Shur et al.

(10) Patent No.: US 9,999,782 B2
(45) Date of Patent: Jun. 19, 2018

(54) ULTRAVIOLET-BASED STERILIZATION

(71) Applicant: Sensor Electronic Technology, Inc., Columbia, SC (US)

(72) Inventors: Michael Shur, Latham, NY (US); Alexander Dobrinsky, Loudonville, NY (US); Maxim S. Shatalov, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days. days.

(21) Appl. No.: 14/747,235

(22) Filed: Jun. 23, 2015

(65) Prior Publication Data

US 2015/0297767 A1 Oct. 22, 2015

Related U.S. Application Data

(63) Continuation-in-part of application No. 13/863,547, filed on Apr. 16, 2013, now Pat. No. 9,061,082.

(60) Provisional application No. 61/624,395, filed on Apr. 16, 2012.

(51) Int. Cl.
*G01J 1/42* (2006.01)
*A61N 5/06* (2006.01)
*A61L 2/00* (2006.01)

(52) U.S. Cl.
CPC .......... *A61N 5/0601* (2013.01); *A61L 2/0047* (2013.01); *A61N 5/0624* (2013.01); *A61N 2005/0609* (2013.01); *A61N 2005/0651* (2013.01); *A61N 2005/0661* (2013.01)

(58) Field of Classification Search
CPC . A61L 2/10; A61L 2/0047; A61N 2005/0609; A61N 2005/0651; A61N 2005/0661; A61N 5/0601; A61N 5/0624
USPC ........................................................ 250/372
See application file for complete search history.

(56) References Cited

U.S. PATENT DOCUMENTS

| 3,992,631 | A | 11/1976 | Harte |
| 5,637,877 | A | 6/1997 | Sinofsky |
| 5,855,203 | A | 1/1999 | Matter |
| 6,110,424 | A | 8/2000 | Maiden et al. |
| 6,171,548 | B1 | 9/2001 | Rose et al. |
| 6,468,428 | B1 | 10/2002 | Nishii et al. |
| 6,468,433 | B1 * | 10/2002 | Tribelski .............. A01M 1/226 210/748.06 |
| 6,524,529 | B1 | 2/2003 | Horton, III |

(Continued)

OTHER PUBLICATIONS

Taeho, J., U.S. Appl. No. 13/863,547 Notice of Allowance, dated Feb. 23, 2015, 11 pages.

(Continued)

*Primary Examiner* — Taeho Jo
(74) *Attorney, Agent, or Firm* — LaBatt, LLC

(57) ABSTRACT

A system for sterilizing at least one surface of an object is provided. The system includes a set of ultraviolet radiation sources and a set of wave guiding structures configured to direct ultraviolet radiation having a set of target attributes to a desired location on at least one surface of the object. The set of wave guiding structures can include at least one ultraviolet reflective surface having an ultraviolet reflection coefficient of at least thirty percent. Furthermore, the system can include a computer system for operating the ultraviolet radiation sources to deliver a target dose of ultraviolet radiation to the at least one target surface of the object.

22 Claims, 13 Drawing Sheets

(56) References Cited

U.S. PATENT DOCUMENTS

| | | |
|---|---|---|
| 6,565,803 B1 | 5/2003 | Bolton et al. |
| 6,592,816 B1 | 7/2003 | Ebel et al. |
| 7,553,456 B2 | 6/2009 | Gaska et al. |
| 7,569,181 B2 | 8/2009 | Golden |
| 7,634,996 B2 | 12/2009 | Gaska et al. |
| 8,277,734 B2 | 10/2012 | Koudymov et al. |
| 8,496,610 B2 | 7/2013 | Levenson et al. |
| 8,506,900 B1* | 8/2013 | Ricciardi ............... A61L 2/04 422/292 |
| 9,006,680 B2 | 4/2015 | Bettles et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 2002/0131699 A1 | 9/2002 | Raguin et al. |
| 2002/0161282 A1 | 10/2002 | Fulghum |
| 2002/0183811 A1 | 12/2002 | Irwin |
| 2003/0086831 A1 | 5/2003 | Horton, III |
| 2003/0232303 A1* | 12/2003 | Black ............... A61N 5/0603 433/29 |
| 2004/0170526 A1 | 9/2004 | Curry et al. |
| 2004/0175288 A1 | 9/2004 | Horton, III |
| 2004/0211888 A1 | 10/2004 | Shur et al. |
| 2005/0151119 A1* | 7/2005 | Jones ............... G02B 5/0226 252/299.1 |
| 2005/0279354 A1 | 12/2005 | Deutsch et al. |
| 2006/0011263 A1 | 1/2006 | Till |
| 2006/0104859 A1 | 5/2006 | Tribelsky |
| 2007/0087167 A1* | 4/2007 | Yoshida ............... G02B 5/0226 428/143 |
| 2007/0187626 A1* | 8/2007 | Gaska ............... A61L 2/10 250/504 R |
| 2007/0196235 A1* | 8/2007 | Shur ............... A23L 3/28 422/62 |
| 2007/0225695 A1* | 9/2007 | Mayer ............... A61B 18/22 606/15 |
| 2007/0276455 A1* | 11/2007 | Fiset ............... A61C 19/066 607/91 |
| 2008/0039768 A1* | 2/2008 | Francis ............... A61M 5/14276 604/8 |
| 2008/0039770 A1* | 2/2008 | Francis ............... A61L 27/306 604/20 |
| 2008/0125838 A1* | 5/2008 | Francis ............... A61M 5/14276 607/92 |
| 2008/0228085 A1* | 9/2008 | Jenkins ............... A61B 1/00071 600/478 |
| 2008/0265179 A1 | 10/2008 | Havens et al. |
| 2009/0032740 A1 | 2/2009 | Smith et al. |
| 2009/0130622 A1 | 5/2009 | Bollinger et al. |
| 2010/0183779 A1 | 7/2010 | Felix |
| 2010/0221155 A1 | 9/2010 | Shimizu et al. |
| 2010/0260644 A1* | 10/2010 | Day ............... A61L 9/205 422/121 |
| 2010/0296971 A1* | 11/2010 | Gaska ............... A61L 2/10 422/62 |
| 2011/0054574 A1 | 3/2011 | Felix |
| 2011/0181191 A1 | 7/2011 | Smith et al. |
| 2011/0212411 A1* | 9/2011 | Sinofsky ............... A61B 18/22 433/29 |
| 2011/0213252 A1 | 9/2011 | Fulghum |
| 2011/0305597 A1* | 12/2011 | Farren ............... A61L 2/10 422/24 |
| 2012/0078118 A1* | 3/2012 | Jenkins ............... A61B 5/065 600/478 |
| 2013/0048545 A1 | 2/2013 | Shatalov et al. |
| 2013/0164836 A1 | 6/2013 | Licamele et al. |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0202962 A1 | 7/2014 | Bilenko et al. |
| 2015/0008167 A1 | 1/2015 | Shturm et al. |
| 2015/0037203 A1* | 2/2015 | Pan ............... H01L 51/502 422/22 |
| 2015/0069270 A1 | 3/2015 | Shur et al. |
| 2015/0165079 A1 | 6/2015 | Shur et al. |
| 2015/0217011 A1 | 8/2015 | Bettles et al. |
| 2016/0074547 A1* | 3/2016 | Dobrinsky ............... A61L 2/10 250/492.1 |

OTHER PUBLICATIONS

Taeho, J., U.S. Appl. No. 13/863,547 Non-Final Rejection, dated Sep. 4, 2014, 21 pages.

Taeho, J., U.S. Appl. No. 15/846,946, Non-Final Rejection1, dated Feb. 12, 2018, 52 pages.

Taeho, J., U.S. Appl. No. 15/856,950, Non-Final Rejection1, dated Feb. 12, 2018, 54 pages.

* cited by examiner

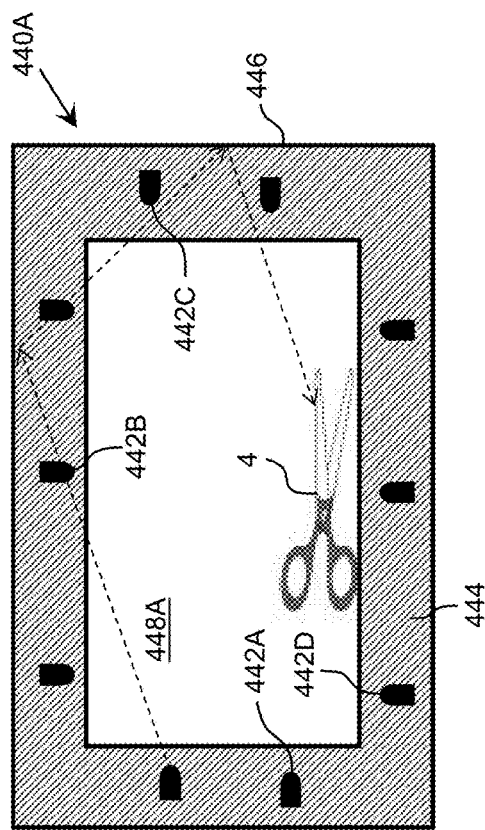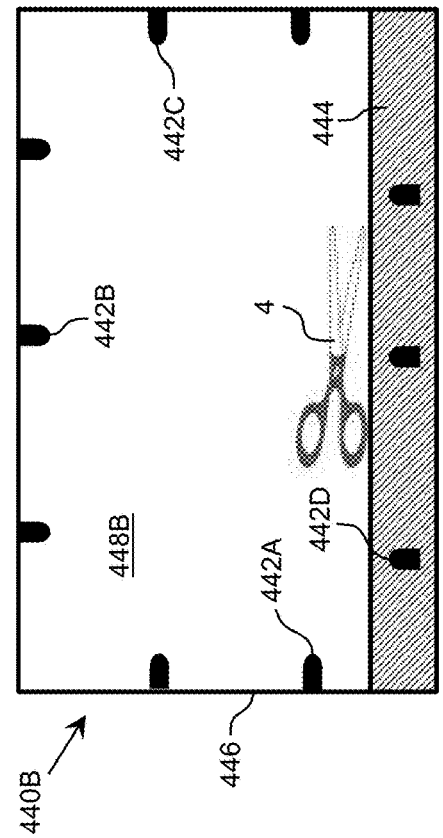

ULTRAVIOLET-BASED STERILIZATION

REFERENCE TO RELATED APPLICATIONS

The current application is a continuation-in-part application of co-pending U.S. application Ser. No. 13/863,547, titled "Ultraviolet-Based Sterilization," which was filed on 16 Apr. 2013, which claims the benefit of co-pending U.S. Provisional Application No. 61/624,395, titled "UV LED Sterilization System," which was filed on 16 Apr. 2012, and which is hereby incorporated by reference.

TECHNICAL FIELD

The disclosure relates generally to ultraviolet-based sterilization, and more particularly, to an improved solution for sterilizing a surface using ultraviolet radiation.

BACKGROUND ART

Ultraviolet water and air purification and sterilization systems are known and have a successful history of development. The main unit of these ultraviolet systems is a source of ultraviolet radiation having wavelength(s) close to the absorption peaks of biologically significant molecules of DNA and proteins. The system can sterilize a medium to a safe condition providing the power of the ultraviolet source and an exposure time are sufficient to destroy the internal biomolecular structure of bacteria, viruses, protozoa and germs.

Known ultraviolet water and air sterilization systems use mercury lamps or deep UV light emitting diodes as a source of ultraviolet radiation. Low-pressure and medium-pressure mercury lamps provide a linear spectrum of radiation with some lines, which wavelengths are in the relative vicinity to a DNA absorption line. A low-pressure mercury lamp with a main peak at 253.4 nm often is used in low-consumption residential water and air purification systems. Medium-pressure mercury lamps with a higher radiation power have a multi-peak radiation spectrum and often are used in municipal systems with medium and high water consumption.

However, the use of mercury lamps has significant drawbacks. For example, mercury lamps are fragile and bulky and mercury is an extremely dangerous element, which implies serious limitations on applications of the mercury-based water purification systems. In particular, mercury lamps are not practical for use in transport and individual systems. Furthermore, a typical operating lifetime of a mercury lamp is less than 10,000 hours. An additional limitation is an inability to adjust or control a radiation spectrum of the mercury lamp. To this extent, the peaks of a mercury lamp do not exactly coincide with the absorption peaks of DNA and proteins, thereby decreasing the sterilization efficiency.

Some approaches have sought to minimize one or more drawbacks of mercury lamp-based sterilization. For example, one approach proposes a handheld ultraviolet water purification system based on a miniature mercury lamp. The design is targeted to overcome the size and portability drawbacks of traditional mercury lamp-based ultraviolet purifying systems. Nevertheless, the need for contact and even steering the sterilizing water with a fragile quartz sleeve with the mercury lamp inside makes the device dangerous for residential applications and not appropriate for transport, field, and portable applications.

SUMMARY OF THE INVENTION

Aspects of the invention provide a system for sterilizing at least one surface of an object. The system includes a set of ultraviolet radiation sources and a set of wave guiding structures configured to direct ultraviolet radiation having a set of target attributes to a desired location on the at least one surface of the object. The set of wave guiding structures can include at least one ultraviolet reflective surface having an ultraviolet reflection coefficient of at least thirty percent. Furthermore, the system can include a computer system for operating the ultraviolet radiation sources to deliver a target dose of ultraviolet radiation to the at least one target surface of the object.

A first aspect of the invention provides a system comprising: a set of ultraviolet radiation sources; a set of wave guiding structures configured to direct ultraviolet radiation having a set of target attributes to a desired location, wherein the set of wave guiding structures includes at least one ultraviolet reflective surface having an ultraviolet reflection coefficient of at least thirty percent; and a computer system for operating the ultraviolet radiation sources to deliver a target dose of ultraviolet radiation to at least one target surface of an object.

A second aspect of the invention provides a system comprising: a set of ultraviolet radiation sources; a set of wave guiding structures configured to direct ultraviolet radiation having a set of target attributes to a desired location, wherein the set of wave guiding structures includes at least one ultraviolet reflective surface having an ultraviolet reflection coefficient of at least thirty percent; and a computer system for sterilizing at least one target surface of an object, wherein the sterilizing includes: removing debris from the at least one target surface of the object using an ultrasonic unit; and delivering a target dose of ultraviolet radiation to the at least one target surface of the object after the removing.

A third aspect of the invention provides a system comprising: a set of ultraviolet radiation sources; a set of wave guiding structures configured to direct ultraviolet radiation having a set of target attributes to a desired location, wherein the set of wave guiding structures includes: a set of ultraviolet reflective surfaces having an ultraviolet reflection coefficient of at least thirty percent, wherein the set of ultraviolet reflective surfaces form an enclosure; and at least one ultraviolet transparent structure forming a movable surface on which an object is placed and located within the enclosure; and a computer system for operating the ultraviolet radiation sources to deliver a target dose of ultraviolet radiation to at least one target surface of the object.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 4A and 4B show illustrative sterilization components according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a system for sterilizing at least one surface of an object. The system includes a set of ultraviolet radiation sources and a set of wave guiding structures configured to direct ultraviolet radiation having a set of target attributes to a desired location on at least one surface of the object. The set of wave guiding structures can include at least one ultraviolet reflective surface having an ultraviolet reflection coefficient of at least thirty percent. Furthermore, the system can include a computer system for operating the ultraviolet radiation sources to deliver a target dose of ultraviolet radiation to the at least one target surface of the object.

A solution described herein can provide a safer design (e.g., mercury lamps do not need to be used in field, transport, and/or portable embodiments), a longer operating lifetime (e.g., ultraviolet light emitting diodes can have a longer operating life than a typical mercury lamp), more effective control of ultraviolet radiation parameters (e.g., wavelength, power, exposure time, radiation area, and/or the like), and/or the like. To this extent, a solution described herein can achieve an improved sterilizing efficiency based on a specific absorption spectra of targeted bio structure(s). As used herein, unless otherwise noted, the term "set" means one or more (i.e., at least one) and the phrase "any solution" means any now known or later developed solution.

Aspects of the invention provide a solution in which surface(s) are sterilized using ultraviolet radiation. To this extent, the ultraviolet radiation can be directed at the surface(s) in such a manner as to harm (e.g., suppress growth of, reduce an amount of, kill, damage, injure, etc.) any organisms that may be present on the surface(s). The organism(s) can comprise any combination of various types of organisms, such as bacteria, viruses, protozoa, biofilms, mold, and/or the like. The discussion herein refers to the sterilization of one or more surfaces. As used herein, "sterilizing" and "sterilization" refer to harming one or more target organisms, and include purification, disinfection, and/or the like. Furthermore, as used herein a "sterilized surface" includes a surface that is devoid of any live organisms, a surface that is devoid of any live targeted organisms (but which may include non-targeted organisms), and a surface that includes some live targeted organism(s), but which is substantially free of such organism(s).

Figure 1:
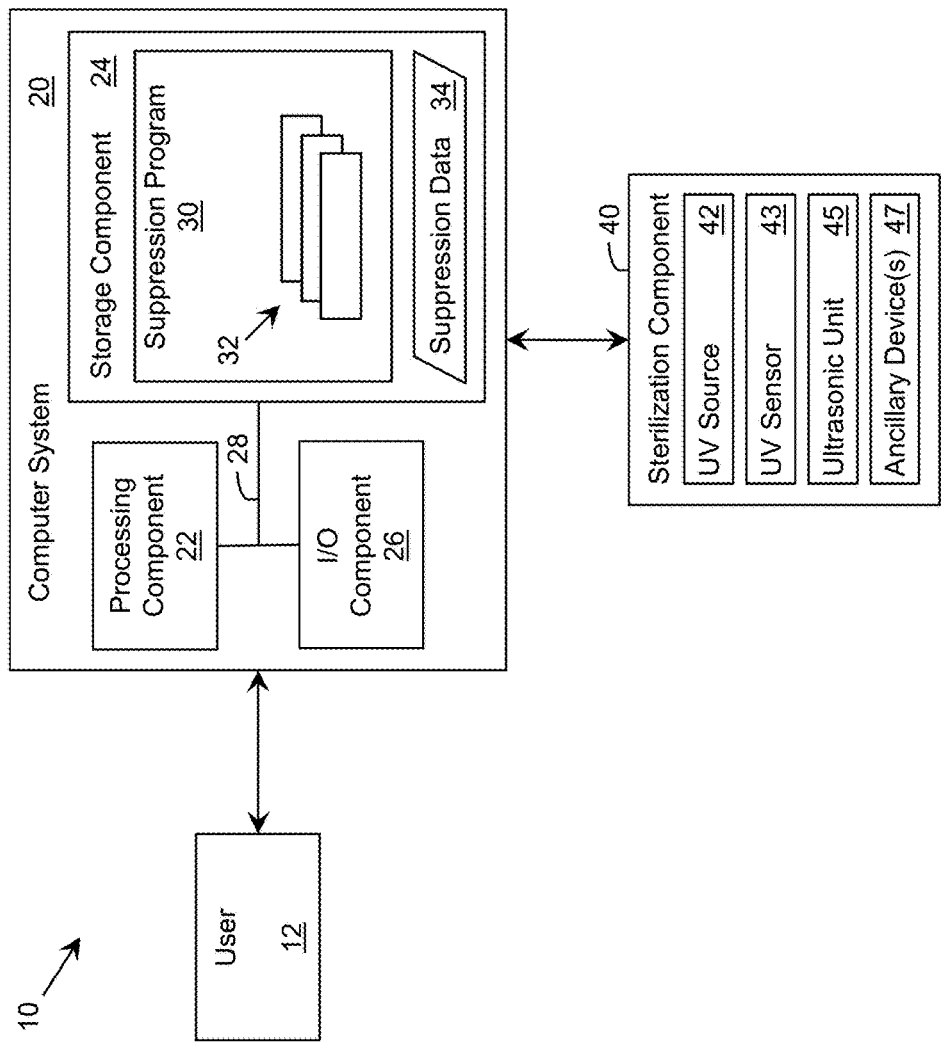
FIG. 1 shows an illustrative environment for sterilizing one or more surfaces using ultraviolet radiation according to an embodiment.

Turning to the drawings, FIG. 1 shows an illustrative environment 10 for sterilizing one or more surfaces using ultraviolet radiation according to an embodiment. To this extent, the environment 10 includes a computer system 20 that can perform a process described herein in order to sterilize one or more surfaces using ultraviolet radiation generated by a sterilization component 40. In particular, the computer system 20 is shown including a suppression program 30, which makes the computer system 20 operable to sterilize one or more surfaces using ultraviolet radiation generated by the sterilization component 40 by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the suppression program 30, which is at least partially fixed in storage component 24. While executing program code, the processing component 22 can process data, which can result in reading and/or writing transformed data from/to the storage component 24 and/or the I/O component 26 for further processing. The pathway 28 provides a communications link between each of the components in the computer system 20. The I/O component 26 can comprise one or more human I/O devices, which enable a human user 12 to interact with the computer system 20 and/or one or more communications devices to enable a system user 12 to communicate with the computer system 20 using any type of communications link. To this extent, the suppression program 30 can manage a set of interfaces (e.g., graphical user interface(s), application program interface, and/or the like) that enable human and/or system users 12 to interact with the suppression program 30. Furthermore, the suppression program 30 can manage (e.g., store, retrieve, create, manipulate, organize, present, etc.) the data, such as suppression data 34, using any solution.

In any event, the computer system 20 can comprise one or more general purpose computing articles of manufacture (e.g., computing devices) capable of executing program code, such as the suppression program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the suppression program 30 can be embodied as any combination of system software and/or application software.

Furthermore, the suppression program 30 can be implemented using a set of modules 32. In this case, a module 32 can enable the computer system 20 to perform a set of tasks used by the suppression program 30, and can be separately developed and/or implemented apart from other portions of the suppression program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the suppression program 30 fixed thereon (e.g., one or more modules 32). However, it is understood that the computer system 20 and the suppression program 30 are only representative of various possible equivalent computer systems that may perform a process described herein. To this extent, in other embodiments, the functionality provided by the computer system 20 and the suppression program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 20 includes multiple computing devices, the computing devices can communicate over any type of communications link. Furthermore, while performing a process described herein, the computer system 20 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols.

As discussed herein, the suppression program 30 enables the computer system 20 to sterilize one or more surfaces using ultraviolet radiation generated by the sterilization component 40. To this extent, the sterilization component 40 can include one or more sources of ultraviolet radiation 42, which can be operated by the computer system 20 to generate ultraviolet radiation having one or more predominant wavelengths in any predetermined radiation band that falls within approximately 200 nanometers to 350 nanometers range of wavelengths. The sterilization component 40 can include any combination of various types of ultraviolet radiation sources 42, such as ultraviolet light emitting diodes (LEDs), ultraviolet laser diodes, mercury lamps (low- and/or medium-pressure), and/or the like. Illustrative ultraviolet LEDs and ultraviolet laser diodes can be formed from compound semiconductors, such as a group III-nitride (e.g., AlingaN—GaN, or the like) based semiconductor. A particular combination of ultraviolet radiation source(s) can be selected based on the desired predominant wavelengths using any solution.

In an embodiment, a predominant wavelength of the ultraviolet radiation generated by the ultraviolet radiation sources 42 can be within a first ultraviolet wavelength region between approximately 250 nanometers and approximately 280 nanometers, which can destroy the DNA/RNA containing organism(s) that may be present. For an ideal air environment, the ultraviolet radiation can have a wavelength between approximately 262 nanometers and approximately 267 nanometers, however, it is understood that the appropriate wavelength(s) will be dependent on the particular mixture of media (e.g., air, water, blood, lymph, and/or the like) in the environment. Additionally, the ultraviolet radiation can include one or more predominant wavelengths in a second ultraviolet wavelength region between approximately 280 nanometers and approximately 360 nanometers, which can prevent the reproduction of DNA/RNA containing organism(s) that may be present. A direct sterilization effect may be possible in a range between approximately 280 nanometers and approximately 320 nanometers, however, other mechanisms and objects of sterilization may be effected by higher wavelengths of ultraviolet radiation. Additionally, the specific wavelength(s) utilized can be selected based on the target organism(s) using any solution.

The computer system 20 can operate the ultraviolet radiation source 42 to deliver a desired dose of radiation for a desired period of time to a target area. The dose can be sufficient to destroy biofilm or reduce formation of biofilm in the target area. In an embodiment, the ultraviolet dose can comprise any ultraviolet dose in a range from approximately 3.5 micro Joules (mJ)/cm$^2$ to approximately 1000 mJ/cm$^2$. In an embodiment, the computer system 20 pulses one or more of the ultraviolet devices in the ultraviolet radiation source 42. For example, when the ultraviolet radiation is in two or more distinct wavelengths, the computer system 20 can pulse the ultraviolet device(s) emitting ultraviolet radiation in one or more of the distinct wavelengths using a distinct pulse duration and/or pulse sequence.

In an embodiment, the sterilization component 40 includes one or more devices for providing feedback for use by the computer system 20 in operating the ultraviolet radiation source 42. For example, the sterilization component 40 can include a set of ultraviolet sensors 43 (e.g., one or more photodetectors, one or more reverse biased ultraviolet LEDs, and/or the like). In this case, the computer system 20 can process data received from the ultraviolet sensors 43 to ensure delivery of a sufficient ultraviolet dose required for a desired level of sterilization. In an embodiment, the ultraviolet radiation source 42 includes a plurality of space distributed pulse-driving ultraviolet emitting devices, which the computer system 20 can independently operate, operate as a plurality of distinct groups of ultraviolet emitting devices, and/or operate in reverse bias as ultraviolet sensors 43. In this case, the ultraviolet radiation source 42 can provide space and/or time distributed ultraviolet radiation to a target surface of an object.

The computer system 20 also can receive data from one or more ancillary devices 47. For example, an ancillary device 47 can include one or more sensors that indicate when the ultraviolet radiation source 42 can be safely operated (e.g., a door to an enclosure is shut), when the ultraviolet radiation source 42 is in position to be operated (e.g., the ultraviolet device(s) are located within a target area), and/or the like. In response to such an indication, the computer system 20 can automatically turn on the ultraviolet radiation source 42. Similarly, in response to a door being opened and/or the like, the computer system 20 can automatically turn off the ultraviolet radiation source 42. The ancillary device(s) 47 also can include one or more devices configured to provide information regarding one or more aspects of the operating environment, treatment environment, target object(s), and/or the like. For example, illustrative ancillary devices 47 can include a flow meter, a power meter, a contamination sensor (e.g., a fluorometer), and/or the like. In an embodiment, the ultraviolet sensor(s) 43, ancillary device(s) 47 (e.g., flow meter, power meter, contamination sensor(s), and/or the like) are implemented as part of an indication and control feedback loop, which enables the computer system 20 to operate a space distributed ultraviolet radiation source 42 to provide a required sterilization ultraviolet dose for unstable current flows, changeable contamination, varying power supply conditions, and/or the like.

The ancillary devices 47 can include various other devices, which are configured to alter one or more aspects of the radiation environment, perform another sterilization, cleaning, and/or purification operation on the target surface(s), and/or the like. For example, the ancillary devices 47 can include a fan for circulating external air into a chamber for air sterilization. Similarly, an environment 10 can include one or more other ancillary devices 47 for performing disinfection including, for example, a heat source for applying heat, a chemical source for chemical sterilization, an ozone source for ozone based disinfection, membrane sterilization of a liquid, and/or the like.

In an embodiment, the sterilization component 40 can include an ultrasonic unit 45. The computer system 20 can operate the ultrasonic unit 45 to remove various debris (e.g., impurities, foreign elements, and/or the like) from the surfaces of a disinfected object (e.g., a device, instrument, tissue, and/or the like) to be sterilized. In an embodiment, the object can be placed (e.g., manually or automatically via a conveyor or the like) in an ultrasonic chamber for cleaning prior to being sterilized in a separate ultraviolet chamber using the ultraviolet radiation. In an alternative embodiment, a chamber is configured for both ultrasonic and ultraviolet cleaning (e.g., the chamber of an ultrasonic cleaner can be configured with an ultraviolet source 42 described herein). In this case, the chamber also can be filled with a cleaning fluid, which can be filtered to remove debris from the chamber. In an embodiment, the computer system 20 can operate the ultraviolet source 42 to irradiate the object while the chamber is filled with cleaning fluid. Filtration of the cleaning fluid can reduce an ultraviolet absorbance of the cleaning fluid.

The sterilization component 40 also can include one or more wave guiding structures, which can be configured to direct ultraviolet radiation having a set of target attributes (e.g., dose, direction(s), and/or the like) to a desired location. The wave guiding structures can include one or more ultraviolet reflective structures and/or one or more ultraviolet transparent structures. An ultraviolet reflective structure can have an ultraviolet reflection coefficient of at least thirty percent for ultraviolet radiation generated by the sterilization component 40. In a more particular embodiment, the ultraviolet reflective structure has an ultraviolet reflection coefficient of at least eighty percent. An illustrative ultraviolet reflective structure can be formed of or covered by highly ultraviolet-reflective aluminum. An ultraviolet transparent structure can comprise any type of structure, which allows a significant amount of the ultraviolet radiation to pass there through. In an embodiment, the ultraviolet transparent structure is formed of a material and has a thickness, which allows at least ten percent of the ultraviolet radiation to pass there through. An illustrative ultraviolet transparent structure can be formed of fused silica. Other illustrative materials include alumina sol-gel glass, alumina aerogel, sapphire, aluminum nitride (e.g., single crystal aluminum nitride), boron nitride (e.g., single crystal boron nitride), and/or the like.

The sterilization component 40 can be configured for various types of applications, in which it is desired to sterilize one or more surfaces of an object. Further aspects of the invention are shown and described in conjunction with illustrative sterilization components configured for various illustrative applications relating to medical sterilization.

Figure 2:
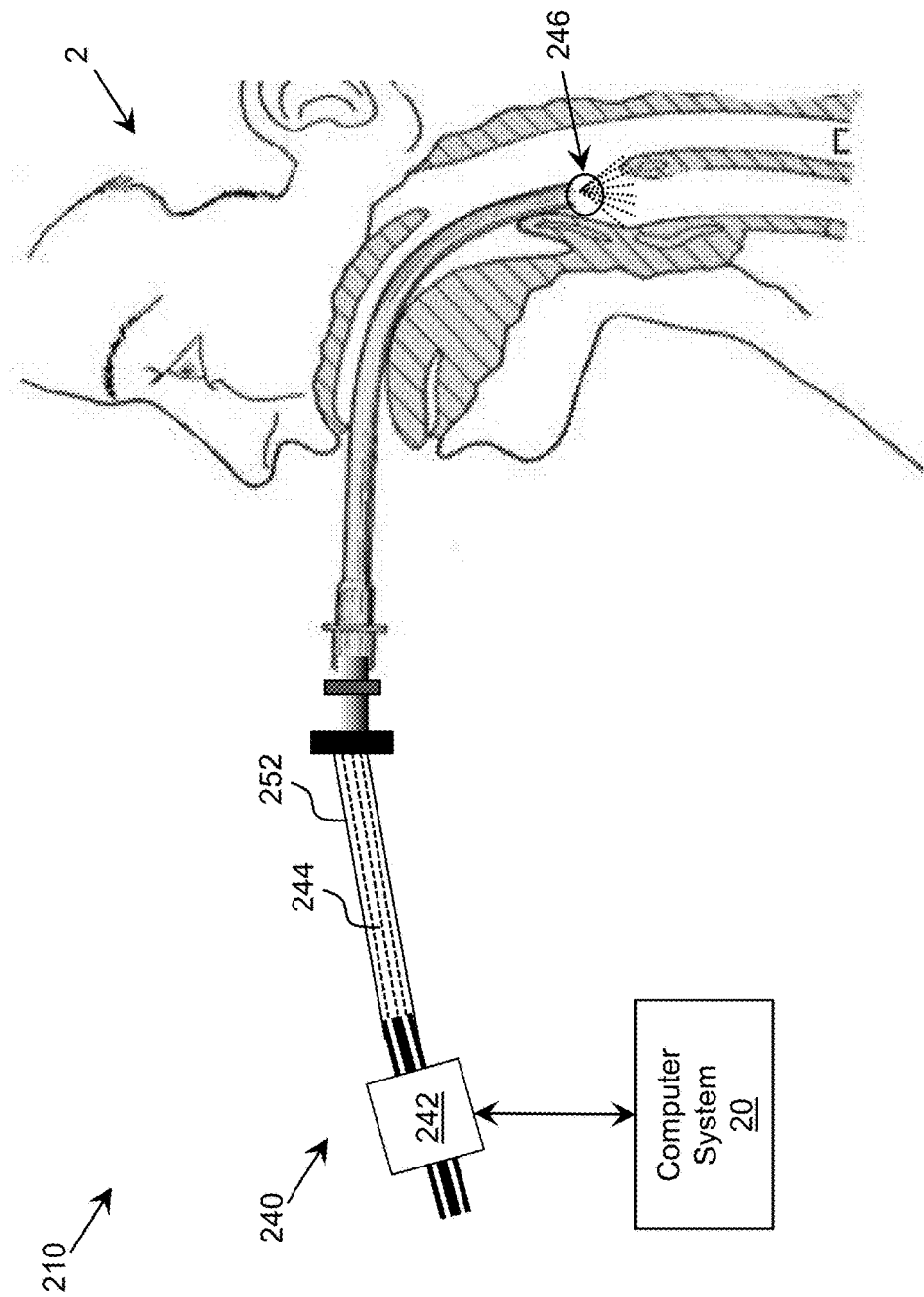
FIG. 2 shows an illustrative environment for performing sterilization within the body of a person according to an embodiment.

For example, FIG. 2 shows an illustrative environment 210 for performing sterilization within the body 2 of a person according to an embodiment. In this case, the computer system 20 can operate a sterilization component 240 to direct ultraviolet light to internal tissues of the body 2. To this extent, the sterilization component 240 can include one or more ultraviolet sources 242, which the computer system 20 can operate to generate ultraviolet radiation having a set of desired attributes. The ultraviolet radiation can be directed to a location 246 within the body 2 by a set of optical fibers 244 formed of an ultraviolet transparent material (e.g., fused silica). When the optical fibers 244 are located in a desired position, the computer system 20 can operate the ultraviolet radiation source(s) 242 in such a manner as to deliver a target dose of ultraviolet radiation to the tissues adjacent to the location 246. In an embodiment, the optical fiber(s) 244 are enclosed within an ultraviolet reflective member 252, which can contain the ultraviolet radiation and increase a dose of the ultraviolet radiation that is delivered at the location 246.

Figure 3B:
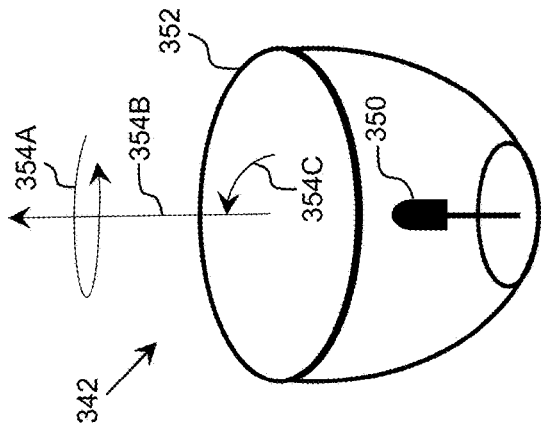
FIGS. 3A and 3B show an illustrative sterilization component according to another embodiment.
Figure 3A:
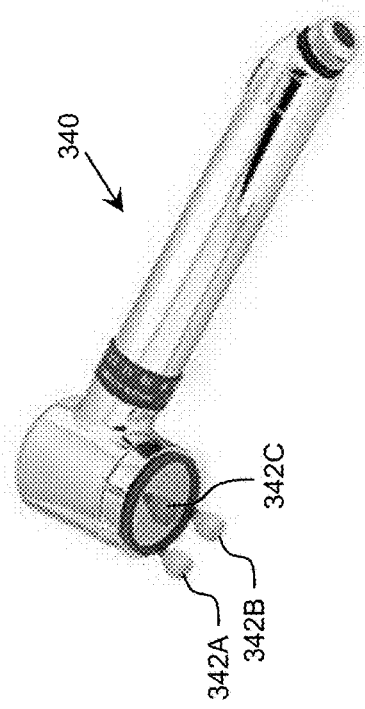

FIGS. 3A and 3B show an illustrative sterilization component 340 according to another embodiment. In this case, the sterilization component 340 is configured to emit collimated ultraviolet light, which can be used to deliver a target dose of ultraviolet radiation to sterilize a set of targeted locations. In FIG. 3A, the sterilization component 340 can comprise a handheld device including a plurality of collimated ultraviolet radiation sources 342A-342C. A user 12 (FIG. 1) can manually locate the sterilization component 340 to a desired location and activate the collimated ultraviolet radiation sources 342A-342C to deliver the target dose of ultraviolet radiation at the targeted location(s).

FIG. 3B shows a more detailed implementation of a collimated ultraviolet radiation source 342 according to an embodiment. The collimated ultraviolet radiation source 342 includes an ultraviolet light emitting diode (LED) 350 and a parabolic reflector 352. The ultraviolet LED 350 can be located at a focal point of the parabolic reflector 352 and emit diffuse ultraviolet light towards the parabolic reflector 352. The diffuse ultraviolet light can reflect off of the parabolic reflector 352, producing a collimated beam of ultraviolet light, which can be directed at a target location to be sterilized. A size of the ultraviolet LED 350 can be relatively small compared to a diameter of the parabolic reflector 352. In an embodiment, the diameter of the parabolic reflector 352 is at least approximately five times greater than a characteristic size of the ultraviolet LED 350. Use of a small UV LED 350 allows for achieving a high degree of collimation, which can be used to target a particular location. In an embodiment, the ultraviolet LED 350 has sub-millimeter dimensions. The parabolic reflector 352 can be formed of/coated with any material highly reflective of ultraviolet light, such as highly ultraviolet-reflective aluminum.

In an embodiment, the collimated ultraviolet radiation source 342 can have one or more movable degrees of freedom 354A-354C. The collimated ultraviolet radiation source 342 can be manually moved by the user 12 (e.g., using a set of manual controls located on a handheld device such as that shown in FIG. 3A), automatically moved by the computer system 20 (FIG. 1), and/or the like. Motion of the collimated ultraviolet radiation source 342 can enable delivery of a known amount of ultraviolet radiation to a particular element of a surface, e.g., by controlling a time required for surface radiation. In an embodiment, the computer system 20 can automatically move a set of collimated ultraviolet radiation sources 342 to provide uniform sterilization by scanning one or more surfaces of an object to be sterilized (e.g., a device, instrument, tissue) with the set of collimated ultraviolet radiation sources 342. In this case, the computer system 20 can operate the set of collimated ultraviolet radiation sources 342 to provide targeted sterilization and/or variable ultraviolet power delivery to various surfaces of the object being sterilized.

A system 10 (FIG. 1) including a sterilization component, such as sterilization components 240 (FIG. 2), 340 (FIG. 3A), can be used in various applications used to sterilize human (or other mammalian) tissue. To this extent, the sterilization component 240, 340 can be implemented as part of any type of system configured to perform any of various types of procedures. Illustrative applications include: a dental diagnostic and/or treatment system for performing dental treatment (e.g., suction, restoration, cleaning, orthodontics, and/or the like); an endoscopic system for performing any type of endoscopy; an ear diagnostic and/or treatment system; a hearing aid; a nasal diagnostic and/or treatment system; a vaginal diagnostic and/or treatment system; a urological diagnostic and/or treatment system; a colorectal diagnostic and/or treatment system (e.g., a colonoscopy); and/or the like. Similarly, an illustrative system 10 can be configured to perform any type of experimental procedure, which can include the sterilization of human/animal tissue.

Aspects of the invention also can be directed to the sterilization of equipment used in various types of applications, such as medical applications. To this extent, FIGS. 4A and 4B show illustrative sterilization components 440A, 440B, respectively, according to embodiments. Each sterilization component 440A, 440B can comprise an enclosure 446, which can have an interior surface that is reflective of ultraviolet radiation in order to increase radiation levels within a corresponding chamber 448A, 448B. Furthermore, one or more interior sides of the enclosure 446 can include an ultraviolet transparent material 444 adjacent thereto. The ultraviolet transparent material 444 can form at least one side of the chamber 448A, 448B within which an object 4 to be sterilized can be placed. In an embodiment, the ultraviolet transparent material 444 forms a surface on which the object 4 is placed for sterilization. In another embodiment, the chamber, such as the chamber 448A, is used for additional sterilization processing (e.g., ultrasonic and/or cleaning fluid) described herein.

Additionally, the interior of the enclosure 446 can include a plurality of ultraviolet light sources 442A-442D, which can be located on each interior side of the enclosure 446. Furthermore, one or more of the ultraviolet light sources 442A-442D can be located within the ultraviolet transparent material 444. In order to sterilize the object 4, the object 4 is placed in the chamber 448A, 448B and the computer system 20 (FIG. 1) can operate the ultraviolet light sources 442A-442D to deliver a desired dose of ultraviolet radiation for a desired period of time. The ultraviolet light sources 442A-442D can be configured to radiate the enclosed object 4 from all sides, including from below the surface on which the object 4 is placed.

Figure 5:
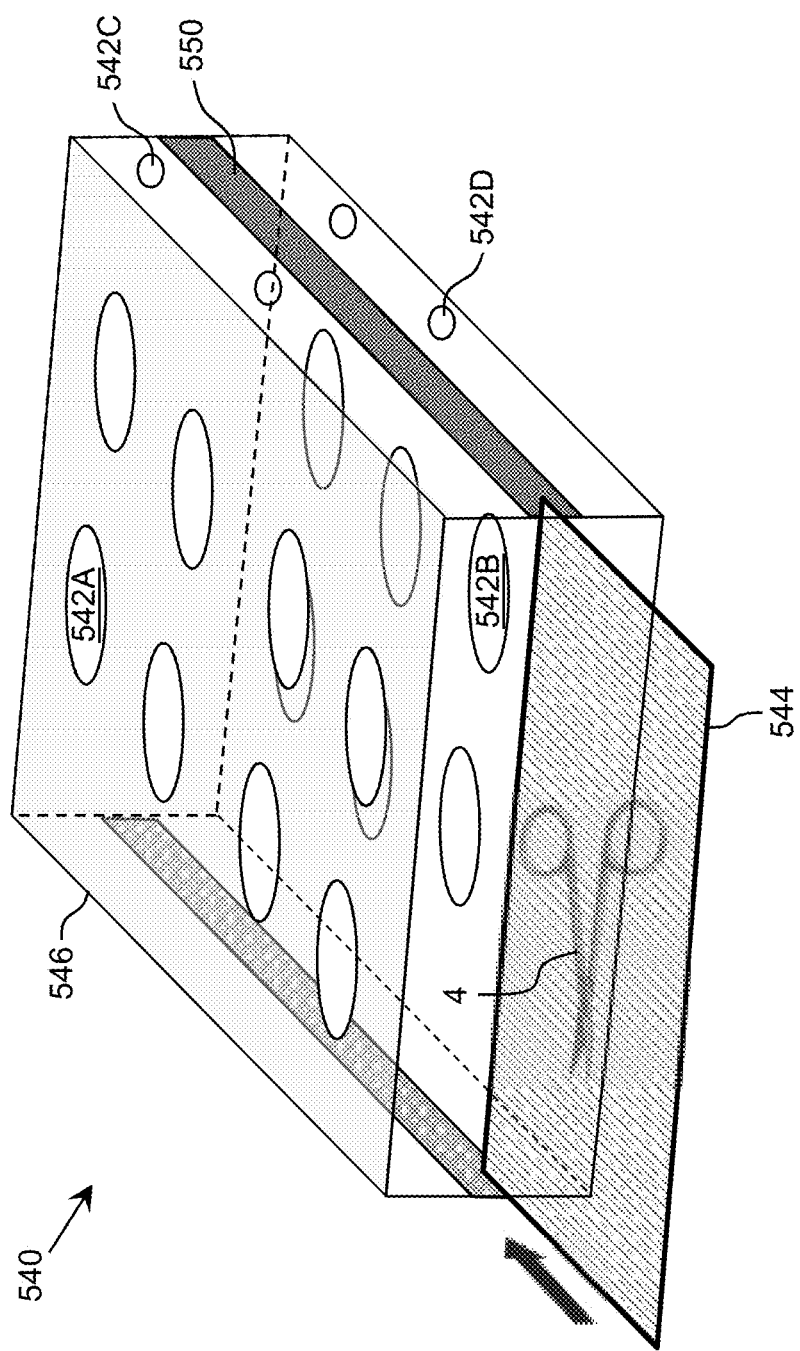
FIG. 5 shows another illustrative sterilization component according to an embodiment.

Various other solutions can be utilized to illuminate an object 4 to be sterilized from multiple directions. For example, FIG. 5 shows another illustrative sterilization component 540 according to an embodiment. In this case, the sterilization component 540 includes an enclosure 546, which can have an ultraviolet reflective interior surface, forming an interior chamber. The interior of the enclosure 546 includes a plurality of ultraviolet light sources 542A-542D. The ultraviolet light sources 542A-542D can be located on each side of the interior of the enclosure 546, one or more of which can include an ultraviolet transparent material similar to that shown in FIGS. 4A and 4B. In an embodiment, one or more of the ultraviolet light sources 542A-542D can be configured to emit ultraviolet light having a primary angle of emission that is different than normal to the corresponding side of the enclosure 546 on which it is located. During sterilization, the computer system 20 (FIG. 1) can operate the ultraviolet light sources 542A-542D to deliver a desired dose for a desired period of time.

The enclosure 546 also is shown including an ultraviolet transparent plate 544 on which an object 4 to be sterilized is placed. The enclosure 546 can include a support structure 550, which enables the ultraviolet transparent plate 544 to be held in a central location within the enclosure 546. In an embodiment, the support structure 550 comprises a railing system or the like, which enables the ultraviolet transparent plate 544 to slide into/out of the enclosure 546. Furthermore, while not shown for clarity, it is understood that the enclosure 546 can include a door to completely seal the enclosure 546. The door can include one or more sensors, a set of ultraviolet light sources, and also can have an ultraviolet reflective interior surface. As illustrated, a side of the enclosure 546 can include ultraviolet light sources, such as ultraviolet light sources 542C, 542D, which are located above and below the support structure 550. In an embodiment, the enclosure 546 can include additional and/or higher power ultraviolet light sources 542A-542D located below the ultraviolet transparent plate 544 to account for a loss of ultraviolet light as it passes through the ultraviolet transparent plate 544.

Figure 6:
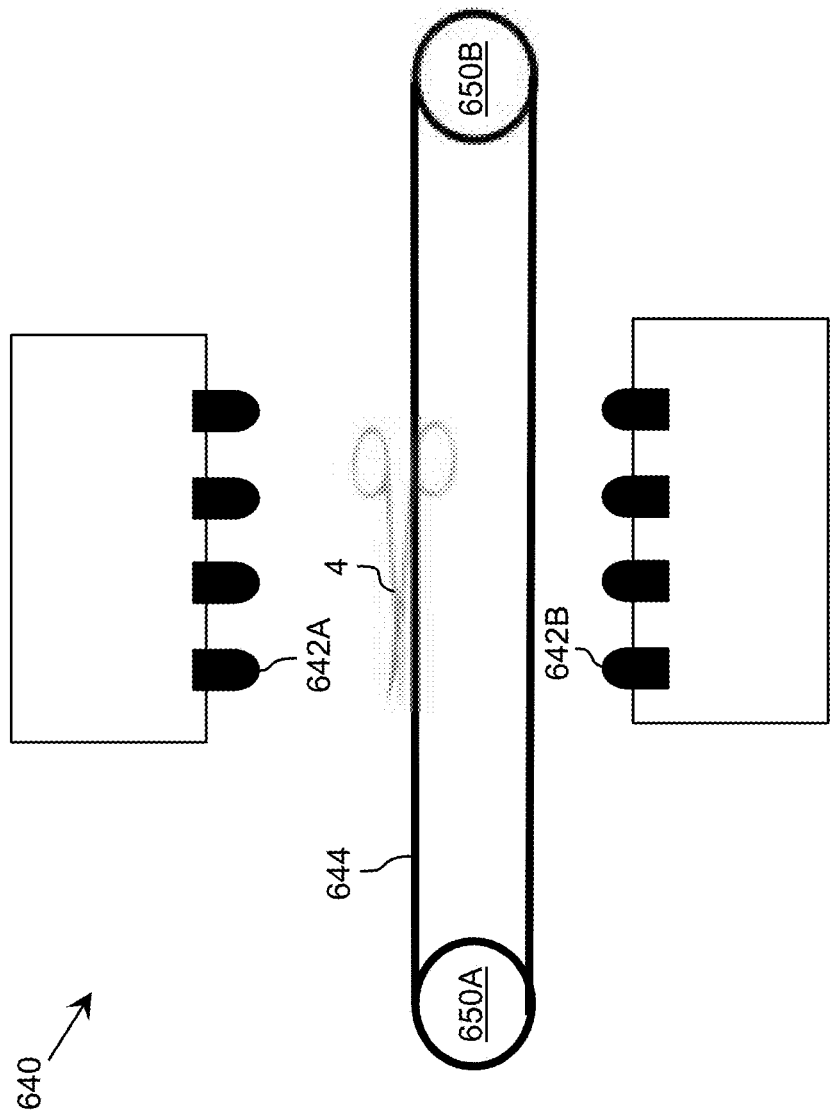
FIG. 6 shows still another illustrative sterilization component according to an embodiment.

FIG. 6 shows still another illustrative sterilization component 640 according to an embodiment. In this case, the sterilization component 640 includes ultraviolet light sources 642A-642B located above and below an ultraviolet transparent belt 644 on which an object to be sterilized can be placed. While not shown for clarity, it is understood that the sterilization component 640 can include one or more side walls having ultraviolet light sources 642A-642B located thereon. The computer system 20 (FIG. 1) can operate the ultraviolet light sources 642A-642B and a set of wheels 650A-650B to move the ultraviolet transparent belt 644 in such a manner to direct a desired ultraviolet dose for a desired amount of time onto the object 4. It is understood that the ultraviolet light sources 642A-642B can be located such that at least a desired ultraviolet dose will be directed toward all sides of the object 4 as it passes through the sterilization component 640. During movement of the object 4 through the sterilization component 640, the computer system 20 can obtain feedback on the sterilization, e.g., by operating one or more of the ultraviolet light sources 642A-642B as an ultraviolet sensor, and make one or more adjustments to the ultraviolet radiation in order to provide a sufficient dose of ultraviolet radiation for a desired amount of sterilization.

Figure 7:
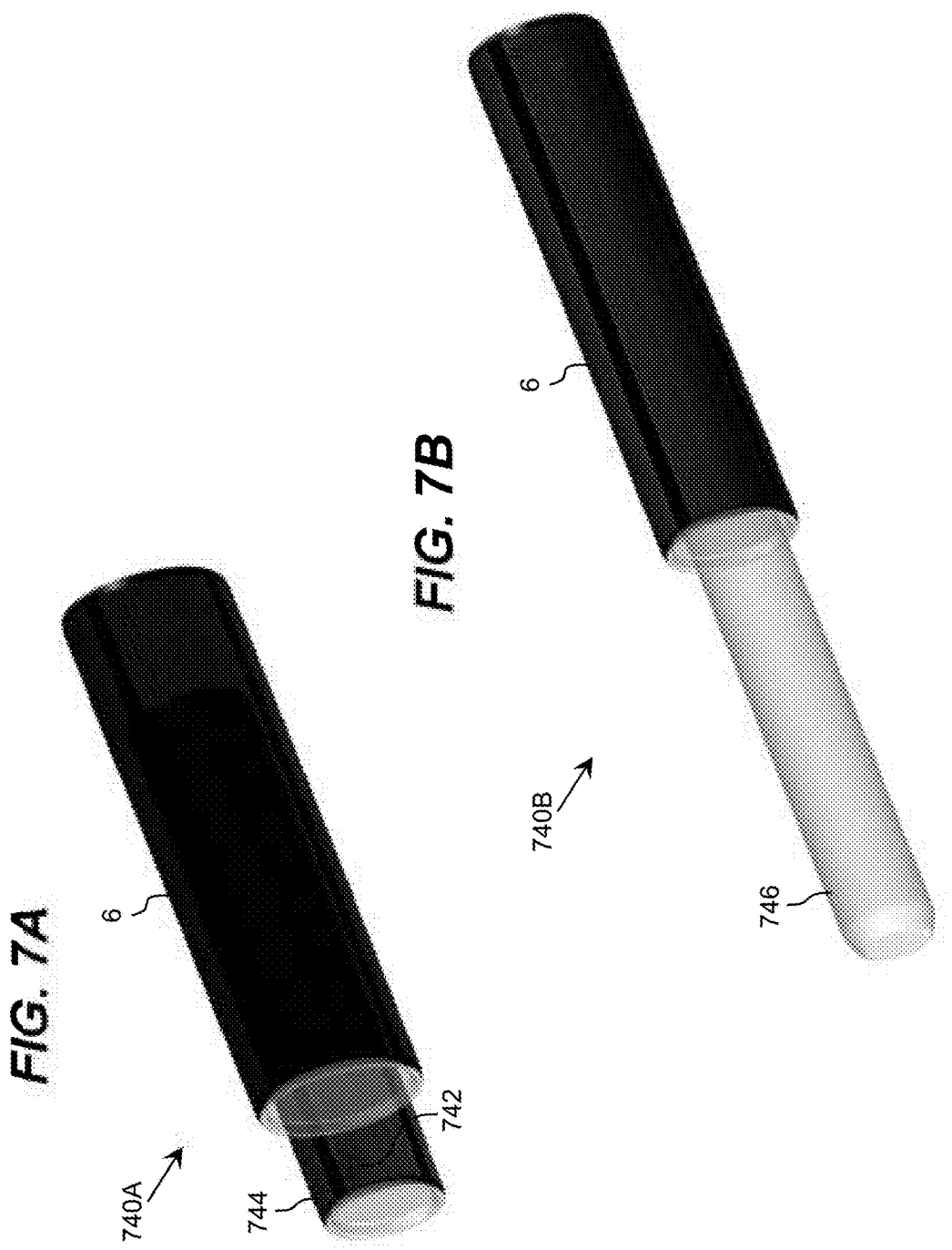
FIGS. 7A and 7B show illustrative sterilization components for sterilizing a tube according to embodiments.

In an embodiment, a sterilization component can be configured to sterilize an object while the object remains in use. For example, the object can comprise a medical tube being used to provide medical treatment to a human (or other animal), e.g., such as that shown in FIG. 2. To this extent, FIGS. 7A and 7B show illustrative sterilization components 740A, 740B, respectively, for sterilizing a tube 6 according to embodiments. Sterilization component 740A includes an ultraviolet transparent tube 744 having a plurality of ultraviolet light sources 742 located thereon. The ultraviolet transparent tube 744 can have a hollow interior, which allows the tube 6 to continue to be used during the sterilization process. Additionally, the ultraviolet transparent tube 744 can have sufficient flexibility to enable the ultraviolet transparent tube 744 to travel along the interior of the tube 6. In this case, the computer system 20 (FIG. 1) can insert the ultraviolet transparent tube 744 directly into the tube 6 and operate the ultraviolet light sources 742 to deliver a desired ultraviolet dose for a desired amount of time onto the interior surface of the tube 6. The ultraviolet transparent tube 744 can contain roughness, texturing, and/or scattering elements on its outer and/or inner surface, which can provide a more uniform ultraviolet distribution of the ultraviolet light emitted by the ultraviolet light sources 742. The sterilization component 740B illustrates use of an ultraviolet transparent optical fiber 746 to deliver ultraviolet radiation directed onto the interior surface of the tube 6. In this case, the ultraviolet radiation can radiate out from the ultraviolet transparent optical fiber 746 in all directions in a substantially uniform manner.

The tube 6 and sterilization components 740A, 740B can be implemented as part of any of various types of medical devices. For example, illustrative medical devices include a respirator, a catheter, a medical drainage system, a blood supply system, an oxygen supply system, an anesthesia system, and/or the like. In each case, the computer system 20 can periodically insert and remove the sterilization component 740A, 740B into one or more tubes 6 of the medical device in order to sterilize the interior of the tube 6 without requiring removal of the tube 6.

Figure 8:
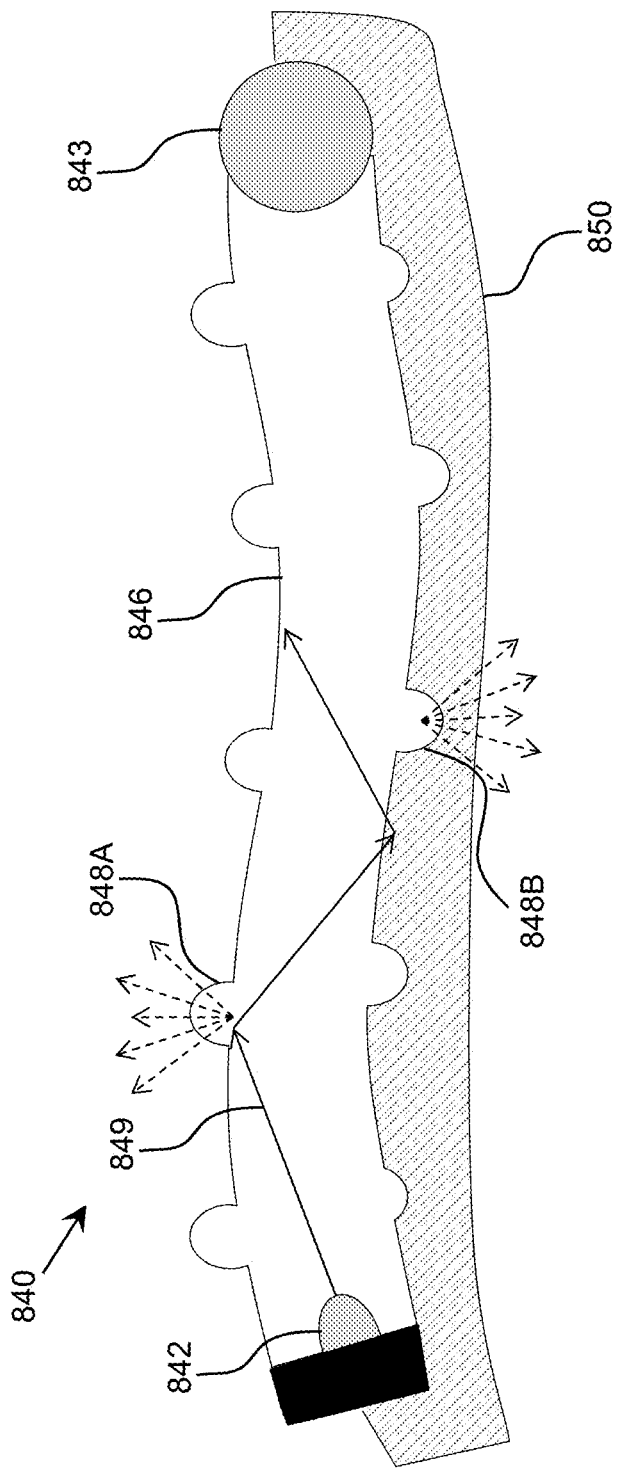
FIG. 8 shows an illustrative sterilization component according to an embodiment.

FIG. 8 shows another illustrative sterilization component 840 according to an embodiment. In this case, the sterilization component 840 includes a flexible wave guiding structure 846 with one or more ultraviolet radiation sources 842 and one or more ultraviolet sensing devices 843. The flexible wave guiding structure 846 can include a socket for attaching each of the ultraviolet radiation sources 842 and/or the ultraviolet sensing devices 843. The flexible wave guiding structure 846 can comprise any shape and/or size. For example, in FIG. 8, the flexible wave guiding structure 846 is a hollow tube. The interior walls of the flexible wave guiding structure 846 can be reflective to ultraviolet radiation due to total internal reflection (TIR) because the index of refraction of the flexible wave guiding structure 846 is larger than the index of refraction of the ambient. In an embodiment, the material of the flexible wave guiding structure 846 can comprise an ultraviolet transparent material, such as a fluoropolymer (e.g., polytetrafluoroethylene (PTFE), fluorinated ethylene propylene (FEP), perfluoro alkoxy (PFA), ethylene tetrafluoroethylene (ETFE)), fused silica, sapphire, and/or the like. The wave guiding structure 846 can also include reflective surfaces so that the ultraviolet radiation 849 is contained within the wave guiding structure 846. A portion of the walls of the wave guiding structure 846 can include a set of diffusive elements (e.g., protrusions) 848 for diffusively radiating the ultraviolet radiation 849 from the ultraviolet radiation source 842. The diffusive elements 848 can be at least partially transparent to ultraviolet radiation, so that the ultraviolet radiation can pass through. The diffusive elements 848 can be formed of a partially transparent material, such as fluorinated ethylene-propylene copolymer (EFEP), fluorinated ethylene propylene (FEP), perfluoro alkoxy (PFA), Fluon® LM-ETFE AH, tetrafluoroethylene hexafluoropropylene vinylidene fluoride (THV), ethylene tetrafluoroethylene (ETFE), FLUON® ETFE, polytetrafluoroethylene (PTFE), and FLUON® LM ETFE. The diffusive elements 848 can also be formed of a partially reflective material, such as, for example, PTFE, expanded PTFE, Teflon®, Valar®, and/or the like. The examples of diffusive elements can include bumps, roughness elements, and/or the like over an otherwise smooth surface on the wave guiding structure 846. In an embodiment, the light emitting source, such as the ultraviolet radiation source 842, is coupled to the wave guiding structure 846 by directly embedding the light emitting source into the wave guiding structure 846, as shown in FIG. 8. In an embodiment, at least fifty percent of the ultraviolet radiation 849 emitted by the ultraviolet radiation source enters the wave guiding structure 846. The method of embedding can include encapsulating the ultraviolet radiation source 842 by placing the ultraviolet radiation source 842 into a melted fluoropolymer and then subsequently cooling. In another embodiment, the ultraviolet radiation source 842 can be attached to the wave guiding structure 846 by a partially transparent epoxy, glue, and/or the like. In an embodiment, the ultraviolet radiation source 842 can include parabolic surfaces, similar to the parabolic reflector 342 shown in FIGS. 3A and 3B, to provide a collimated beam of ultraviolet radiation. The entire ultraviolet radiation source 842, including a parabolic reflector and any other corresponding optical components attached to the ultraviolet radiation source 842, can be incorporated into the wave guiding structure 846. Examples of other optical components can include, for example, lenses, additional reflective surfaces, and/or the like. In an embodiment, the parabolic reflector can include comprise polished aluminum that is ultraviolet reflective and has an ultraviolet radiation reflection coefficient of at least eighty percent.

The sterilization component 840 can also include a spine element 850 with a cavity for the flexible wave guiding structure 846. The flexible wave guiding structure 846 can be placed within the spine element 850. The spine element 850 is flexible and deformable in order to at least partially preserve the shape of the wave guiding structure 846. The spine element 850 can be formed of a flexible and deformable material, such as aluminum, steel, or copper wire, rubber, flexible plastic, and/or the like. FIG. 8 shows the UV radiation 849 diffusively radiating from the diffusive elements 848A, 848B. The diffusive element 848B is configured to protrude into the spine element 850. It is understood that, in an embodiment, the spine element 850 can be UV absorbing not include diffusive element 848B. The flexibility of the wave guiding structure 846 is used to direct the diffused ultraviolet radiation 849 towards a target area, and the spine element 850 is used to at least partially preserve the shape of the wave guiding structure 846. Although it is not shown, the wave guiding structure 846 can also include a set of optic fibers, such as the optic fibers 244 in FIG. 2. For example, the set of optic fibers can be a part of the diffusive elements 848. In another embodiment, the sterilization component 840 can include an ultraviolet reflective chamber for enclosing the wave guiding structure 846 and the spine element 850. The ultraviolet reflective chamber can be used to contain the diffused ultraviolet radiation 849 from the wave guiding structure 846 and increase the dose of ultraviolet radiation delivered to a target area.

Figure 9:
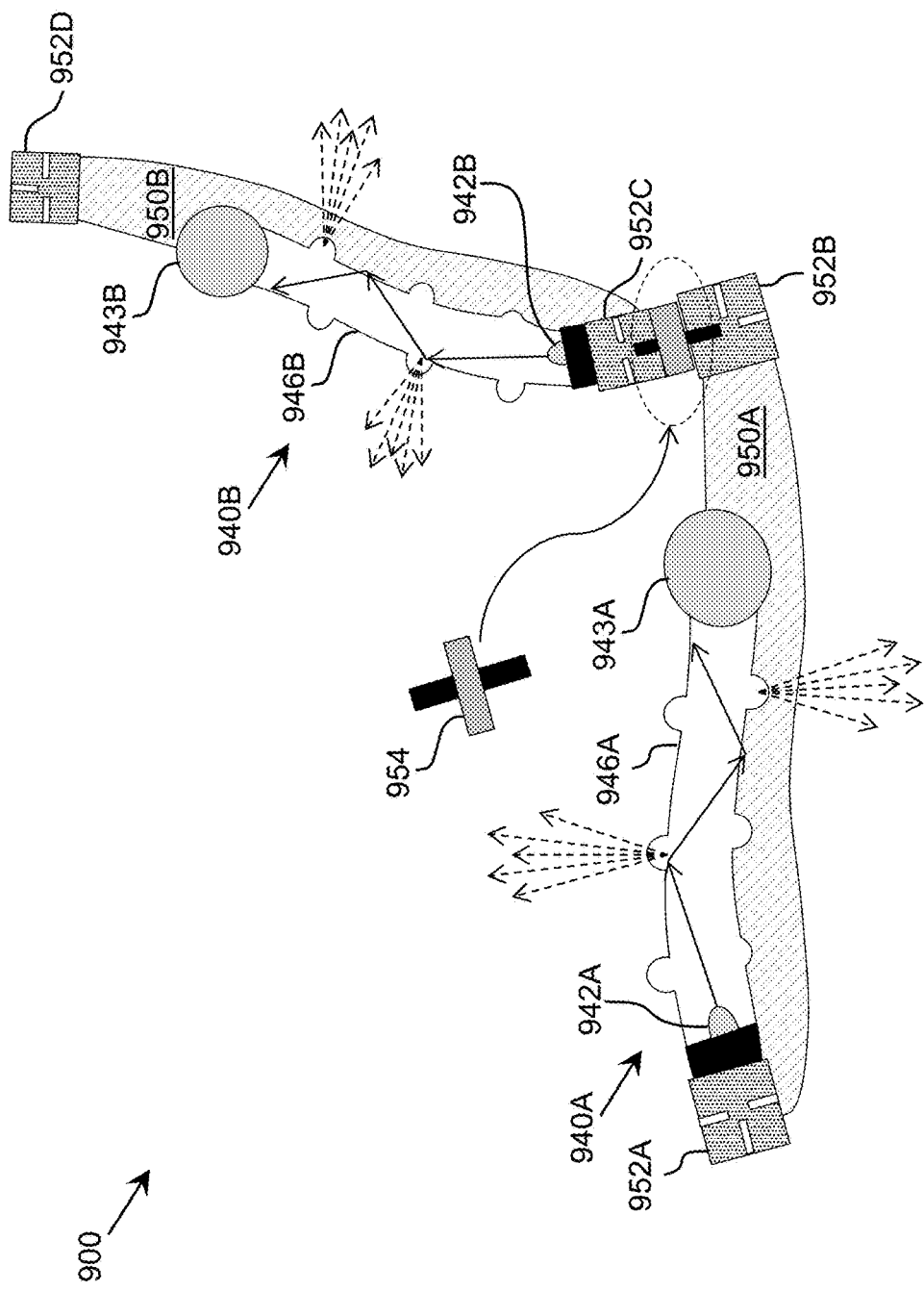
FIG. 9 shows an illustrative system including connected sterilization components according to an embodiment.

In an embodiment, multiple sterilization components can be connected to one another in order to increase the overall ultraviolet radiation delivered to a target area. For example, FIG. 9 shows an illustrative system 900 that includes a first sterilization component 940A connected to a second sterilization component 940B. It is understood that any number of sterilization components can be connected. The sterilization components 940A, 940B can include all the features of the sterilization component 840 described above in FIG. 8, such as one or more ultraviolet radiation sources 942A, 942B, one or more ultraviolet sensing devices 943A, 943B, flexible wave guiding structures 946A, 946B, spine elements 950A, 950B, and/or the like, respectively. However, in order to connect the first sterilization component 940A to the second sterilization component 940B, each sterilization component 940A, 940B can include a set of connection units. That is, the first sterilization component 940A can include a first connection unit 952A and a second connection unit 952B located at each end of the spine element 950A and the second sterilization component 940B can include a first connection unit 952C and a second connection unit 952D located at each end of the spine element 950B. The second connection unit 952B of the first sterilization component 940A is connected to the first connection unit 952C of the second sterilization component 940B via a connector 954. In an embodiment, each of the connection units 952A-D can comprise a power outlet design in order to provide an electrical connection between each of the sterilization components 940A, 940B.

Figure 10:
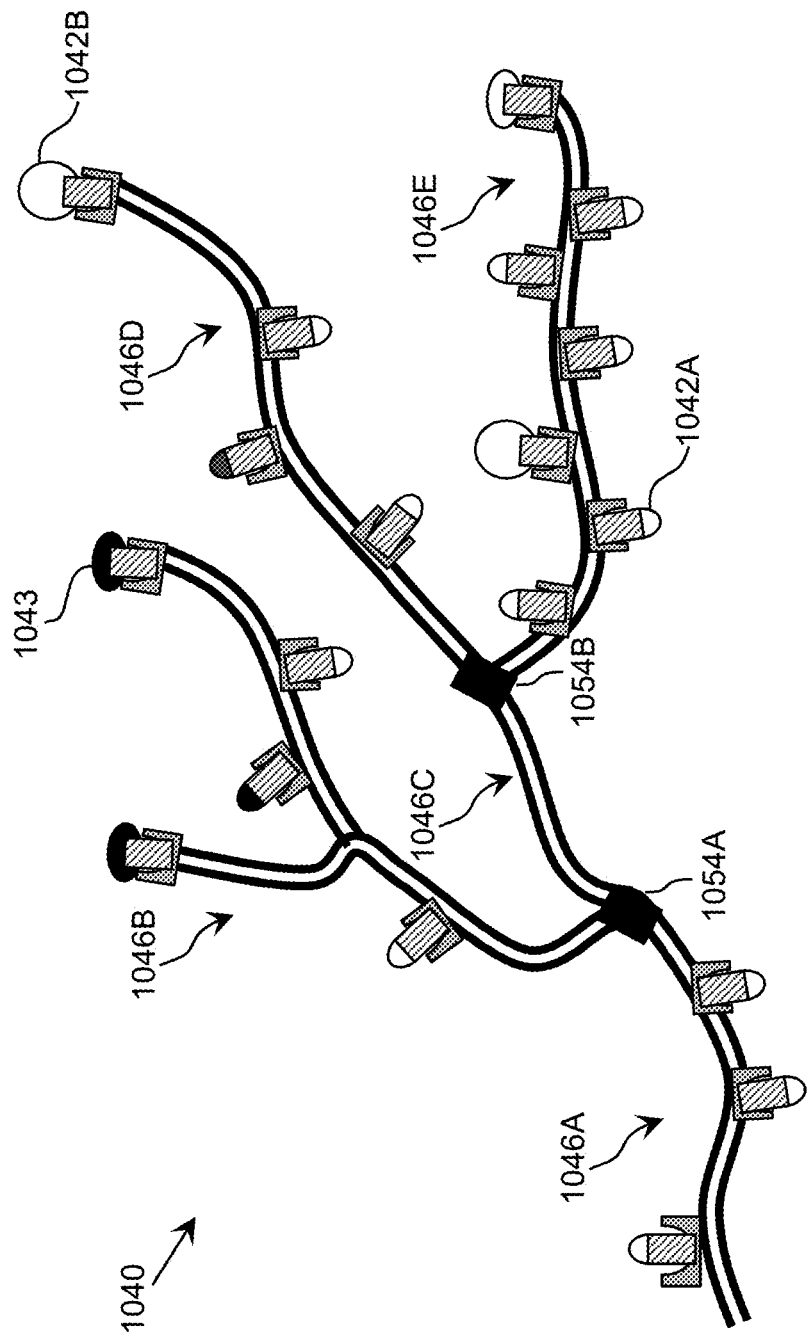
FIG. 10 shows an illustrative sterilization component according to an embodiment.

Turning now to FIG. 10, another illustrative sterilization component 1040 according to an embodiment is shown. The sterilization component 1040 can include a plurality of flexible wave guiding structures 1046A-E that are connected by flexible connectors 1054A, 1054B to form a tree-like configuration. The flexible connectors 1054A, 1054B can comprise a material that is similar to the material used for the flexible wave guiding structures 1046A-E. The flexible connectors 1054A, 1054B can include wiring to deliver power to the ultraviolet radiation sources 1042A, 1042B and/or the set of ultraviolet radiation sensors 1043. The flexible connectors 1054A, 1054B can be similar to the connection units 952A-D and connectors 954 described in FIG. 9. The plurality of flexible wave guiding structures 1046A-E are configured to support the set of ultraviolet radiation sources 1042A, 1042B and a set of ultraviolet radiation sensors 1043. The set of ultraviolet radiation sources 1042A, 1042B can include any type of ultraviolet radiation sources. That is, the sterilization component 1040 can include a first type of ultraviolet radiation source 1042A and a second type of ultraviolet radiation source 1042B, and each type of ultraviolet radiation source can include a different intensity, efficiency, light angular distribution, and/or the like. The set of ultraviolet radiation sensors 1043 can be configured to measure the radiation reflected from the surface of the target area to be disinfected and used as feedback to adjust the dose of ultraviolet radiation provided by the set of ultraviolet radiation sources 1042A, 1042B.

Figure 11:
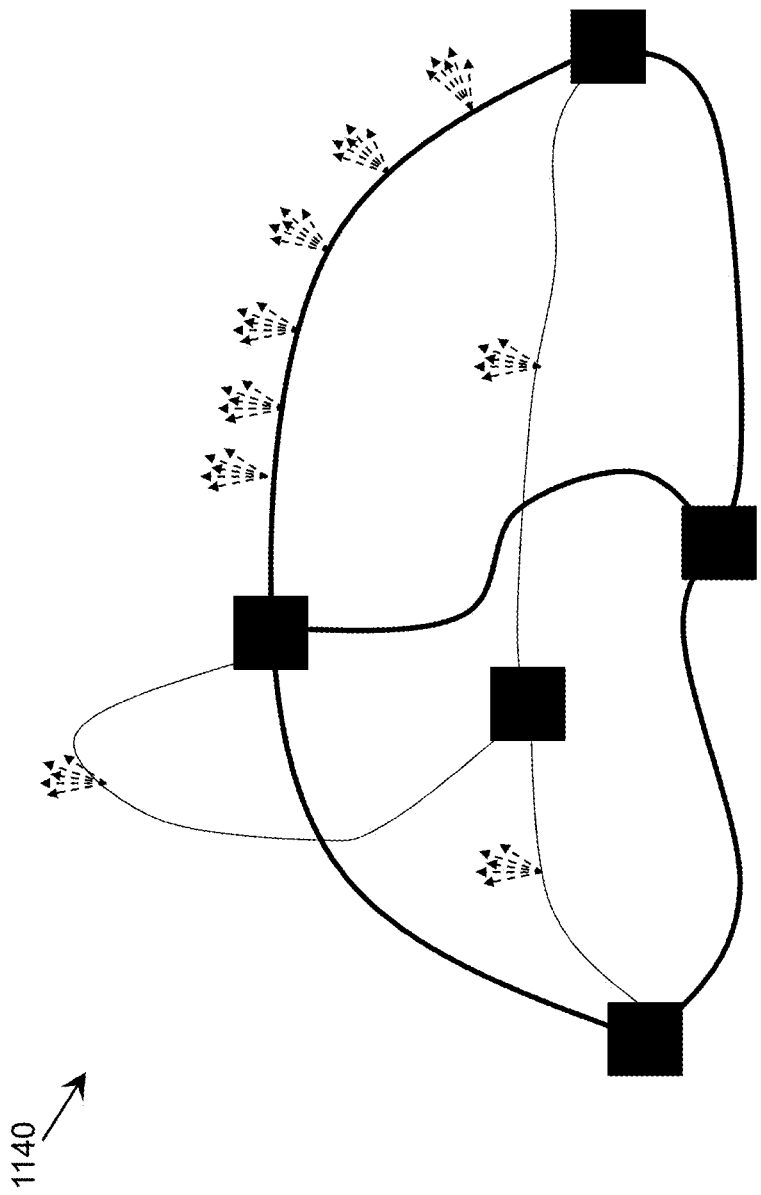
FIG. 11 shows an illustrative sterilization component according to an embodiment.
Figure 12:
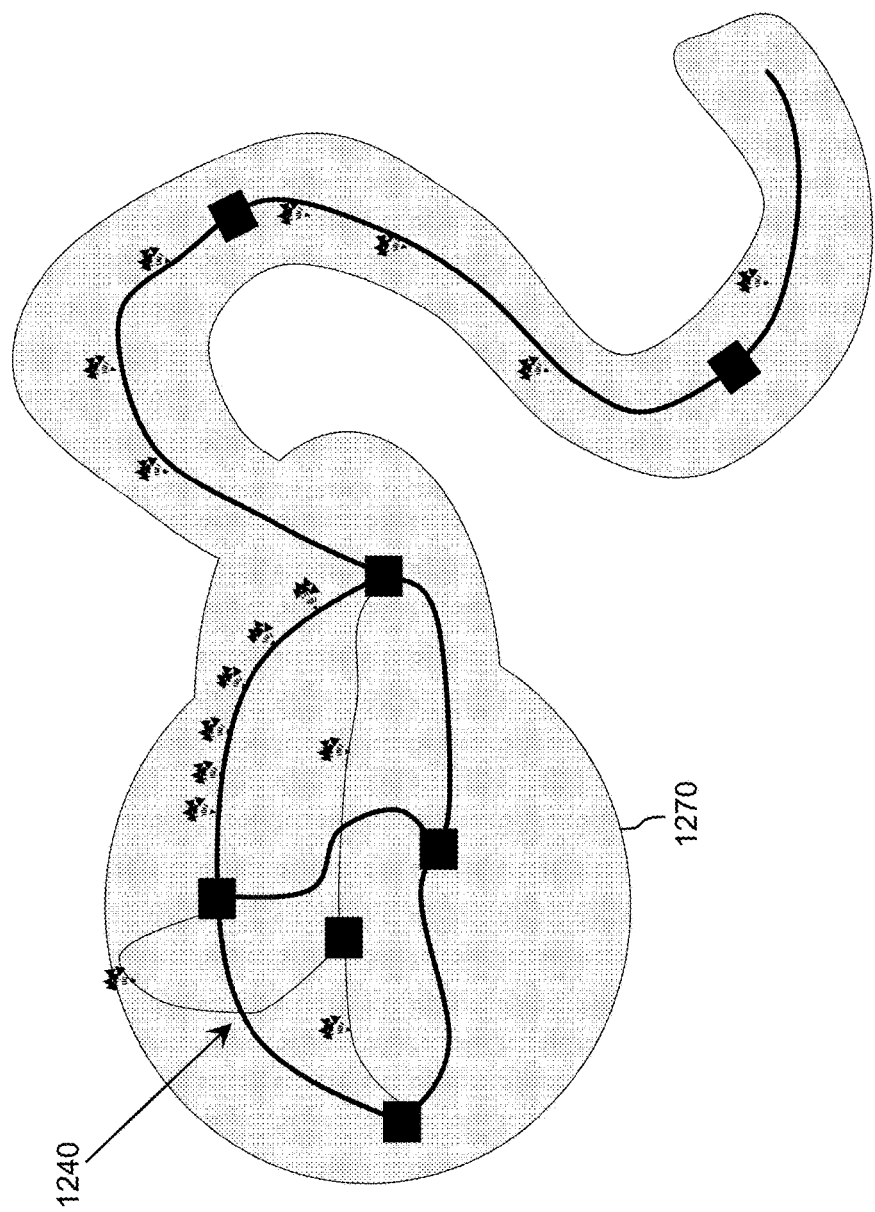
FIG. 12 shows an illustrative sterilization component according to an embodiment.

FIG. 11 shows another illustrative sterilization component 1140 according to an embodiment. The sterilization component 1140 is similar to the sterilization component 1040 shown in FIG. 10, with a configuration that is different from the tree-like configuration shown in FIG. 10. The sterilization component 1140 includes a 3-dimensional preserving mesh configuration for a different ultraviolet radiation distribution from the sterilization component 1040 shown in FIG. 10. Regardless, it is understood that the sterilization components 1040, 1140 shown in FIGS. 10-11 can have any configuration and the configuration can depend on the target area to be disinfected. Turning now to FIG. 12, another illustrative sterilization component 1240 according to an embodiment is shown. The sterilization component 1240 includes all the features of the sterilization components 1040, 1140 shown in FIGS. 10, 11 and is placed within a cavity of a complex shaped body 1270 in order to disinfect the interior surfaces of the body 1270.

Figure 13:
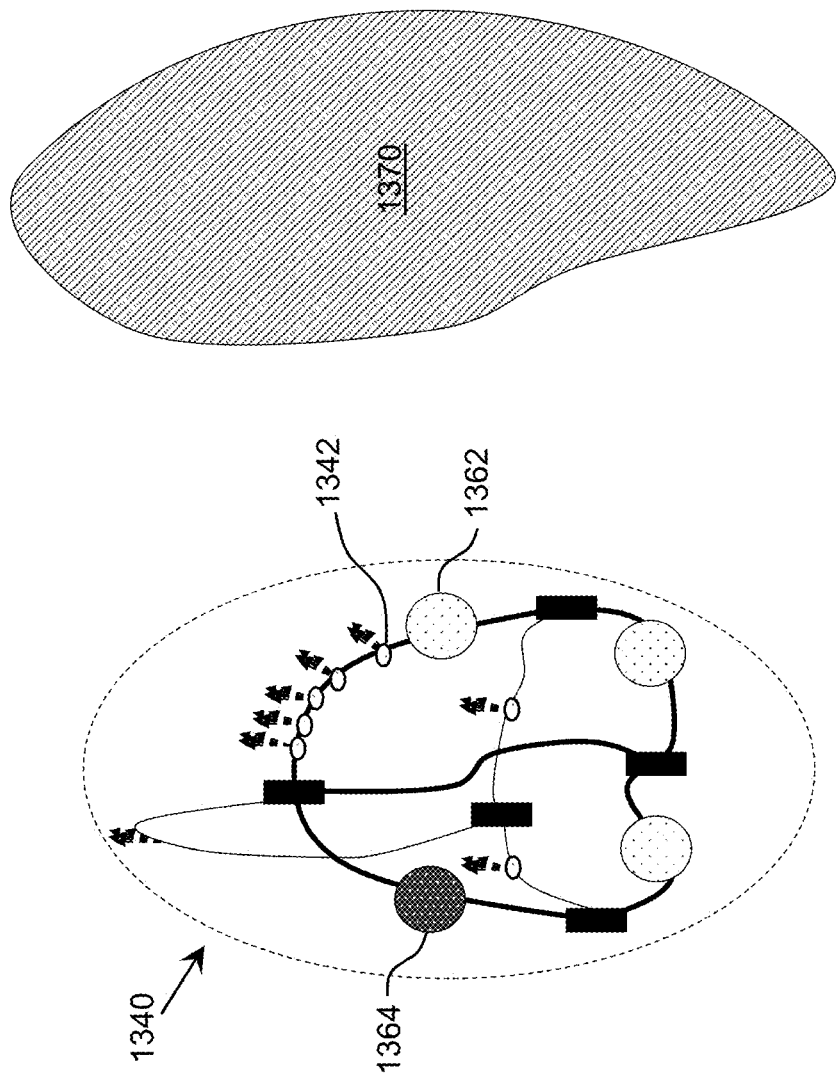
FIG. 13 shows an illustrative sterilization component according to an embodiment.

Turning now to FIG. 13, another illustrative sterilization component 1340 according to an embodiment is shown. In this embodiment, the sterilization component 1340 is similar to the sterilization components 1040, 1140, 1240 shown in FIGS. 10-12. However, the sterilization component 1340 can also include a proximity sensor 1362 that measures the distance between the sterilization component 1340 and the target area 1370 to be disinfected. The characteristics of the ultraviolet radiation generated by the set of ultraviolet radiation sources 1342 of the sterilization component 1340 can be modified based on feedback from the proximity sensor 1362. For example, the angular distribution, the intensity, the activation/deactivation, and/or the like of the ultraviolet radiation can be modified based on the measurements from the proximity sensor 1362. The sterilization component 1340 can also have a switch 1364 for manually activating or deactivating the ultraviolet radiation.

While primarily shown and described in conjunction with medical sterilization applications, it is understood that embodiments can be directed to the sterilization of various types of objects and locations. For example, embodiments can be directed to sterilization of various types of cabinets and/or compartments in household areas, such as a bathroom cabinet, a refrigerator, a produce containing compartment, cosmetic or toiletry bags, a wallet, and/or the like. Similarly, embodiments can be directed to sterilization of a protective suit, such as a hazardous material protection suit, a space suit, and/or the like.

While shown and described herein as a method and system for sterilizing an object, it is understood that aspects of the invention further provide various alternative embodiments. For example, in one embodiment, the invention provides a computer program fixed in at least one computer-readable medium, which when executed, enables a computer system to sterilize the object. To this extent, the computer-readable medium includes program code, such as the suppression program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the suppression program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for sterilizing an object. In this case, the generating can include configuring a computer system, such as the computer system 20 (FIG. 1), to implement the method of sterilizing the object. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
   a plurality of ultraviolet radiation sources;
   a set of flexible wave guiding structures configured to support the plurality of ultraviolet radiation sources and to direct ultraviolet radiation having a set of target attributes to a desired location, wherein the set of flexible wave guiding structures includes at least one reflective surface and at least one transparent surface, wherein the set of flexible wave guiding structures includes a plurality of at least partially transparent diffusive elements protruding from a surface of the set of flexible wave guiding structures, the plurality of diffusive elements configured to provide a uniform distribution of ultraviolet radiation directed out of the set of flexible wave guiding structures, and wherein each flexible wave guiding structure is supported by a spine element configured to preserve a shape of the flexible wave guiding structure;
   a set of connecting units located at each end of the spine element, the set of connecting units configured to connect the set of flexible wave guiding structures and provide an electrical connection between the set of flexible wave guiding structures; and
   a computer system for operating at least some of the plurality of ultraviolet radiation sources to deliver a target dose of ultraviolet radiation to the desired location, operating at least one of the plurality of ultraviolet radiation sources as an ultraviolet sensor to measure the ultraviolet radiation, and adjusting at least one aspect of the operating the at least some of the plurality of ultraviolet radiation sources based on data acquired using the at least one of the plurality of ultraviolet radiation sources operating as an ultraviolet sensor, wherein the computer system selects the at least one of the plurality of ultraviolet radiation sources to operate as an ultraviolet sensor based on the desired location.

2. The system of claim 1, wherein the set of flexible wave guiding structures includes a flexible hollow tube.

3. The system of claim 1, wherein the plurality of ultraviolet radiation sources operate at at least two peak wavelengths, wherein a first peak wavelength is between 250 nanometers and 280 nanometers and a second peak wavelength is between 280 nanometers and 360 nanometers.

4. The system of claim 1, wherein at least one of the plurality of ultraviolet radiation sources delivers ultraviolet radiation in a distinct pulse sequence.

5. The system of claim 1, wherein at least one of the connecting units is configured to connect more than two flexible wave guiding structures.

6. The system of claim 1, wherein the set of flexible wave guiding structures are formed of a fluoropolymer.

7. The system of claim 1, wherein the set of wave guiding structures forms a tree-like configuration.

8. The system of claim 1, wherein the set of wave guiding structures forms a three-dimensional mesh configuration.

9. The system of claim 1, further comprising a set of proximity sensors for measuring a distance to the desired location, wherein the adjusting is further based on the distance.

10. The system of claim 1, wherein at least one the plurality of ultraviolet radiation sources includes a parabolic surface for generating a collimated beam of ultraviolet radiation from ultraviolet radiation generated by the at least one of the plurality of ultraviolet radiation sources, wherein the parabolic surface has an ultraviolet reflection coefficient of at least eighty percent, and wherein the operating includes adjusting a direction of the collimated beam of ultraviolet radiation based on the desired location.

11. A system comprising:
    a plurality of ultraviolet radiation sources;
    a set of flexible wave guiding structures configured to support the plurality of ultraviolet radiation sources and to direct ultraviolet radiation having a set of target attributes to a desired location of an interior of a tube, wherein the set of flexible wave guiding structures includes a plurality of at least partially transparent diffusive elements protruding from a surface of the set of flexible wave guiding structures, the plurality of diffusive elements configured to provide a uniform distribution of ultraviolet radiation directed out of the set of flexible wave guiding structures, and wherein each flexible wave guiding structure is supported by a spine element configured to preserve a shape of the flexible wave guiding structure;
    a set of connecting units located at each end of the spine element, the set of connecting units configured to connect the set of flexible wave guiding structures and provide an electrical connection between the set of flexible wave guiding structures, wherein at least one connecting unit located at an end of the spine element includes an ultraviolet radiation source; and
    a computer system for operating the set of wave guiding structures and the plurality of ultraviolet radiation sources to deliver a target dose of ultraviolet radiation to the desired location of the interior of the tube while the tube is in use.

12. The system of claim 11, wherein the plurality of ultraviolet radiation sources operate at at least two peak wavelengths, wherein a first peak wavelength is between 250 nanometers and 280 nanometers and a second peak wavelength is between 280 nanometers and 360 nanometers.

13. The system of claim 11, wherein at least one of the connecting units is configured to connect more than two flexible wave guiding structures.

14. The system of claim 11, wherein a material of the spine element includes at least one of: aluminum, copper, steel or plastic.

15. The system of claim 11, wherein the set of flexible wave guiding structures are formed of a fluoropolymer.

16. The system of claim 11, wherein the spine element includes wiring to supply power to the plurality of ultraviolet radiation sources.

17. The system of claim 11, wherein at least one of the plurality of ultraviolet radiation sources delivers ultraviolet radiation in a distinct pulse sequence.

18. The system of claim 11, further comprising a set of proximity sensors for measuring a distance to the desired location.

19. A system comprising:
   a plurality of ultraviolet radiation sources;
   a plurality of flexible wave guiding structures configured to support the plurality of ultraviolet radiation sources and to direct ultraviolet radiation having a set of target attributes to a desired location, wherein each of the plurality of flexible wave guiding structures includes a plurality of at least partially transparent diffusive elements protruding from a surface of each of the plurality of flexible wave guiding structures, the plurality of diffusive elements configured to provide a uniform distribution of ultraviolet radiation directed out of each of the plurality of flexible wave guiding structures, and wherein each of the plurality of flexible wave guiding structures includes at least one reflective surface and at least one transparent surface to the ultraviolet radiation, wherein each flexible wave guiding structure of the plurality of flexible wave guiding structures includes at least one of the plurality of ultraviolet radiation sources coupled thereto, and wherein each flexible wave guiding structure is supported by a spine element configured to preserve a shape of the flexible wave guiding structure;
   a set of connecting units located at each end of the spine element, the set of connecting units configured to connect the set of flexible wave guiding structures and provide an electrical connection between the set of flexible wave guiding structures; and
   a computer system for operating the ultraviolet radiation sources to deliver a target dose of ultraviolet radiation to the desired location.

20. The system of claim 19, wherein at least one of the connecting units are configured to connect more than two flexible wave guiding structures.

21. The system of claim 19, wherein the at least one reflective surface of each of the plurality of flexible wave guiding structures is an inner surface of each of the plurality of flexible wave guiding structures.

22. The system of claim 19, wherein the plurality of wave guiding structures form a tree-like structure.

* * * * *